(12) United States Patent
Sun

(10) Patent No.: US 7,074,190 B2
(45) Date of Patent: Jul. 11, 2006

(54) NON-INVASIVE APPARATUS SYSTEM FOR MONITORING DRUG HEPATOXICITY AND USES THEREOF

(75) Inventor: Dehchuan Sun, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 180 days.

(21) Appl. No.: 10/679,741

(22) Filed: Oct. 6, 2003

(65) Prior Publication Data

US 2004/0073121 A1 Apr. 15, 2004

(30) Foreign Application Priority Data

Oct. 9, 2002 (TW) .............................. 091123292 A

(51) Int. Cl.
*A61B 5/00* (2006.01)

(52) U.S. Cl. ...................... 600/485; 600/500

(58) Field of Classification Search ................ 600/485, 600/490, 493–496, 500–503, 300
See application file for complete search history.

(56) References Cited

U.S. PATENT DOCUMENTS

| 5,140,991 | A | * | 8/1992 | Niwa .......................... 600/500 |
|---|---|---|---|---|
| 5,730,138 | A | | 3/1998 | Wang |
| 6,616,613 | B1 | * | 9/2003 | Goodman .................... 600/504 |
| 2003/0125631 | A1 | * | 7/2003 | Amano ........................ 600/500 |
| 2004/0059202 | A1 | * | 3/2004 | Mori ........................ 600/300 |
| 2004/0267141 | A1 | * | 12/2004 | Amano et al. .............. 600/500 |
| 2005/0143628 | A1 | * | 6/2005 | Dai et al. .................... 600/300 |

FOREIGN PATENT DOCUMENTS

| EP | 0359206 | * 9/1989 | ................ 600/500 |
|---|---|---|---|
| EP | 0818175 | 1/1998 | |
| TW | 363404 | 1/1987 | |
| WO | 0130231 | 5/2001 | |

OTHER PUBLICATIONS

Yang, M.W., et al. "Continuous, on-line, real-time spectral analysis of SAP signals during cardiopulmonary bypass." *American Physiological Society* (1995) pp. H2329-H2335, 1995.

DeBoer, R.W., et al. "Hemodynamic fluctuations and baroreflex sensitivity in humans: a beat-to-beat model." *American Physiological Society* (1987) pp. H680-H689.

* cited by examiner

*Primary Examiner*—Robert Nassar
(74) *Attorney, Agent, or Firm*—Ladas & Parry

(57) ABSTRACT

The invention relates to a non-invasive apparatus system for monitoring drug hepatotoxicity, and its uses in monitoring drug-induced hepatotoxicity and abnormal liver function.

18 Claims, 12 Drawing Sheets

NON-INVASIVE APPARATUS SYSTEM FOR MONITORING DRUG HEPATOXICITY AND USES THEREOF

FIELD OF THE INVENTION

The invention relates to a non-invasive apparatus system for monitoring drug hepatotoxicity, and its uses in monitoring drug-induced hepatotoxicity and abnormal liver function.

BACKGROUNDS OF THE INVENTION

The world population has a tendency towards aging. In view of the increasing population suffering from chronic diseases caused by aging, pharmaceutical companies around the world have been developing new drugs for treating chronic diseases to improve the quality of life for those suffering from chronic diseases. However, many drugs which are being, or soon to be, marketed are usually accompanied by an acute liver side effect emerging in some patients (patients with minor symptoms would stop taking the drugs, and those with severe symptoms would undergo a liver transplant, and at a critical stage might die) and were banned. Since these spontaneous liver side effects are related to the special constitution of patients or the inter-reaction between drugs, and the occurrence rate is extremely low (generally lower than 0.1%), it is unpredictable to doctors and patients, and even to pharmaceutical companies during the clinical trial period of the drug. Recalling a drug which is therapeutically beneficial to the majority of patients but posing severe safety concern to very few patients, is one of the dilemma the medical industry facing today.

The medical industry is at a loss on the acute liver side effect. The pharmaceutical companies normally apply animal studies and human trials to test the hepatotoxicity of a new drug during its developing period, and only the ones with low hepatotoxicity will be further investigated and allowed to be marketed. However there are still limitations on these hepatotoxicity-evaluating tests. First, hepatotoxicity are sometimes tested for interactions between the drug candidate and other approved drugs prior to marketing. However, a newly marketed drug might be taken by the patients with other drugs which are not included in the primary clinical trial drugs and may cause unpredictable side effects as a result. Furthermore, the number of the patients of the clinical trials is generally limited, such as in the range of dozens, hundreds, or thousands, since the acute severe liver cases occur at a rate of 0.1% or less, statistically there will be no acute liver poisoning case observed in the human trial with less than one thousand people, and only 10 acute cases in a clinical trial of 10,000 people. Even if these special cases (or other adverse effects with occurrence rate of less than 1%) were observed in the trial, they are generally excluded from the normal analysis and marked with "unknown causes" on the clinical reports, and will not stop the drug of being marketed. The largest pharmaceutical company in the world, Pfizer Inc., has recalled a new diabetic drug Rezulin recently. Prior to recall, the annual revenue of Rezulin was about 1 billion US dollars and was being taken by nearly 1 million diabetic patients worldwide. Food and Drug Administration recalled Rezulin after receiving several liver toxicity cases (a few dozens of patients were dead or needed liver transplants). In addition to the loss of the drug development cost and new drug revenue, a recall-induced litigation and legal liabilities could amount to hundreds of millions of dollars.

U.S. Pat. No. 5,730,138 disclosed a method which utilized a set of equipments to measure the blood pressure fluctuation of a patient's artery, then calculate frequencies of harmonic waves corresponding to the heart beat base frequency by Fourier Transform method. This United States patent also claims that the first harmonic wave obtained in the frequency analysis can indicate the blood circulating status and the function of the liver, and other harmonic waves (second, third harmonics, etc.) represent other organs of the body. However, the purpose of that case is mainly on the diagnosis of patients' blood circulating system, and that when determining whether the patient's liver function is normal, it needs to compare the characteristics of patients' liver harmonic wave with normal people to determine if the liver function is normal.

The prior art described above has not disclosed or suggested the prevention of acute liver side effects induced by drugs. For reducing the occurrence rate of acute liver side effects, the pharmaceutical companies often ask patients to have a blood test every month or every two months to examine the liver function, which includes measuring the concentrations of the liver enzymes (e.g., AST [also named SGOT], ALT [also named SGPT] and bilirubin) in the blood. When one of the three values is higher than the normal value and reaches a certain level (usually two to three fold higher than the normal value), the physician will instruct the patient to stop taking the drug. Since acute liver toxicity can occur within days or weeks, the monthly or bi-monthly test can only reduce the occurrence rate but cannot effectively prevent it from happening. Furthermore, the liver function test from blood samples not only is costly, but also causes pain (when drawing blood samples) and inconvenience (back and forth to the clinics) to the patients.

The inventor has found that a non-invasive pressure sensor and the equipment system containing the same can be used to detect the blood pressure pulse baseline of the patients before taking the drug, and the changes of the blood pressure pulse wave during the drug administration. The characteristics of the pulse changes can be detected in the clinical trial of the drug. The inventor has further found that regularly monitoring the changing value of the blood pressure wave characteristics during the drug taking period can detect some symptoms such as the liver poisoning or inflammation happening in the early period. Since the administrated drug will be degraded or transformed by the liver before being excreted, if the drug causes toxicity or damage to the liver cells and causes inflammation, the amount of blood flowing to the liver artery will be increased over the normal range to cope with the new oxygen demand and support the regeneration of the liver cells. Furthermore, swollen liver cells and their peripheral organs caused by the poisoning and inflammation will increase the resistance of the internal liver blood flow and hinder the blood flowing from the gastrointestinal vein through the portal vein into the liver, and result in portal hypertension and splanchnic venous bed pressure increase. Under these circumstances, to reduce the increased blood pressures, autonomic nervous system and regional tissue cells may release the vasodilating factors to expand blood vessels. Since the veins and arteries of the human body are centered in the heart and are into-connected to form a network, arterial pressure waveforms will be correspondingly changed by all the alterations on blood dynamic described above. Therefore, the measurement of arterial pressure waveforms and the monitoring of their altered amount can be the theoretical and technological basis for preventing acute liver side effects caused by drugs. The exact characteristics and the amount altered of the blood pressure waveforms (whether in the normal range caused by typical drug effects or abnormal caused by liver side effects) can be measured by analyzing the experimental results of human clinical trials. Accordingly, the abnormal liver functional symptom can be monitored, and an alarm and advice can be provided to the patient for stop taking the drug. The present invention is based on comparing the blood pressure waveform changes before and after the patients take the drug of the same persons, but not comparing a patient with other normal persons. In addition, the system apparatus of the present invention is easy to use at home, and the acquired data can be transmitted to the doctors via a variety of communication methods (e.g., telephone, internet, radio). The system apparatus of the present invention can reduce the medical costs and the pain and inconvenience of the patients.

SUMMARY OF THE INVENTION

The present invention provides an apparatus device and method for monitoring the liver function during the period of patients taking drug to prevent an acute liver poisoning side effect. The apparatus can be used by patients at home and provide alarm in the early stage of the liver side effect, and therefore, it has the effect and purpose of preventing severe liver poisoning cases from occurring.

DETAILED DESCRIPTION OF THE INVENTION

The present invention relates to an apparatus system for measuring hepatotoxicity or abnormal liver function by using non-invasive techniques, which comprises (a) a sensor for measuring artery blood pressure waveforms to generate electric waveforms representing the artery blood pressure waveforms; and (b) an analyzer for receiving the electric waveforms from (a), wherein waveform shape parameters (including the number of peaks, major peak point, major valley point, minor peak point(s), and minor valley point), time parameters, pressure parameters, oblique angle parameters, area parameters, and/or ratio parameters in the electric waveforms can be calculated by a mathematical method.

Figure 2:
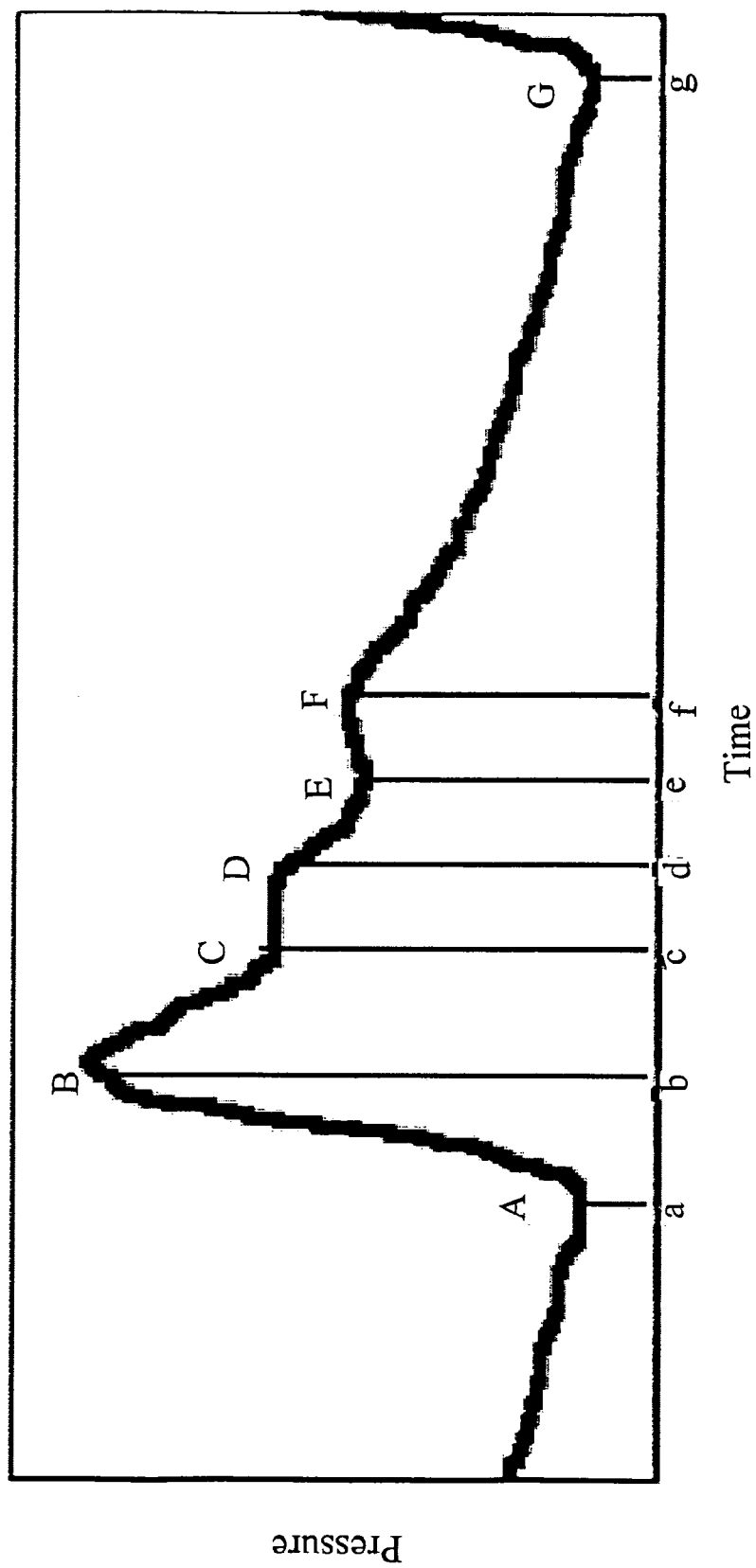
FIG. 2 illustrates an example of the blood pressure waveform of the hand radial artery of a normal person.

According to the apparatus system of this present invention, the parameters of blood pressure waveforms of the hand radial artery of normal persons illustrated in FIG. 2 can be determined and calculated by known mathematical formulas, specific computer programs, or the human brain. The parameters include wave shape parameters (including the number of peaks, major peak point, major valley point, minor peak point, and minor valley point), time parameters (T1 to T6), pressure parameters (P1 to P6), oblique angle parameters (D1 to D9), area parameters (A1 to A10), and/or ratio parameters (RT1 to RT5, RP1 to RP2, RA1 to RA5). The hand radial artery blood pressure waveform is a periodic wave; the general characteristic of the wave shape can be explained by well-known physiology and blood dynamics. The starting point (the A point in FIG. 2) of the blood pressure waveform is a small wave front caused by atria starting to contract, which is normally observed in young persons and those with highly elastic arteries and heart valves. After the contraction of the atria, the ventricles start to contract, and the blood is quickly ejected through the aorta. The blood pressure waveform ascends sharply (from point A to point B). Point B represents the major wave peak and is also the maximum value of the blood pressure waveform, which is generally called the systolic pressure. Since the aorta is an elastic tissue, it will quickly expand when the high pressure blood passes through, but when the ejection of blood comes to an end (point C), the elasticity will cause a slight contraction of the vessel and form a second wave peak on the wave form. When the ventricle has finished the ejection, the aorta valve between the ventricle and the aorta is suddenly shut off and the blood flow is stopped (point E, also called dicrotic notch). However, the blood that is originally back flowing to the ventricle through aorta will be cut off as well. This blood flow will hit against the aorta valves and then flow back to aorta, and cause the blood pressure to rise once again and form the third wave (point F). Thereafter, the heart remains in a relaxed status and the blood will gradually flow from the aorta to the arteries and the branches thereof, the blood pressure will keep descending till the lowest point (G), which is also called diastolic pressure. Point G in FIG. 2 is the starting point of the next heart beat or blood pressure wave, which is equal to point A in the previous wave, and the blood pressure wave will repeat continually.

Figure 3:
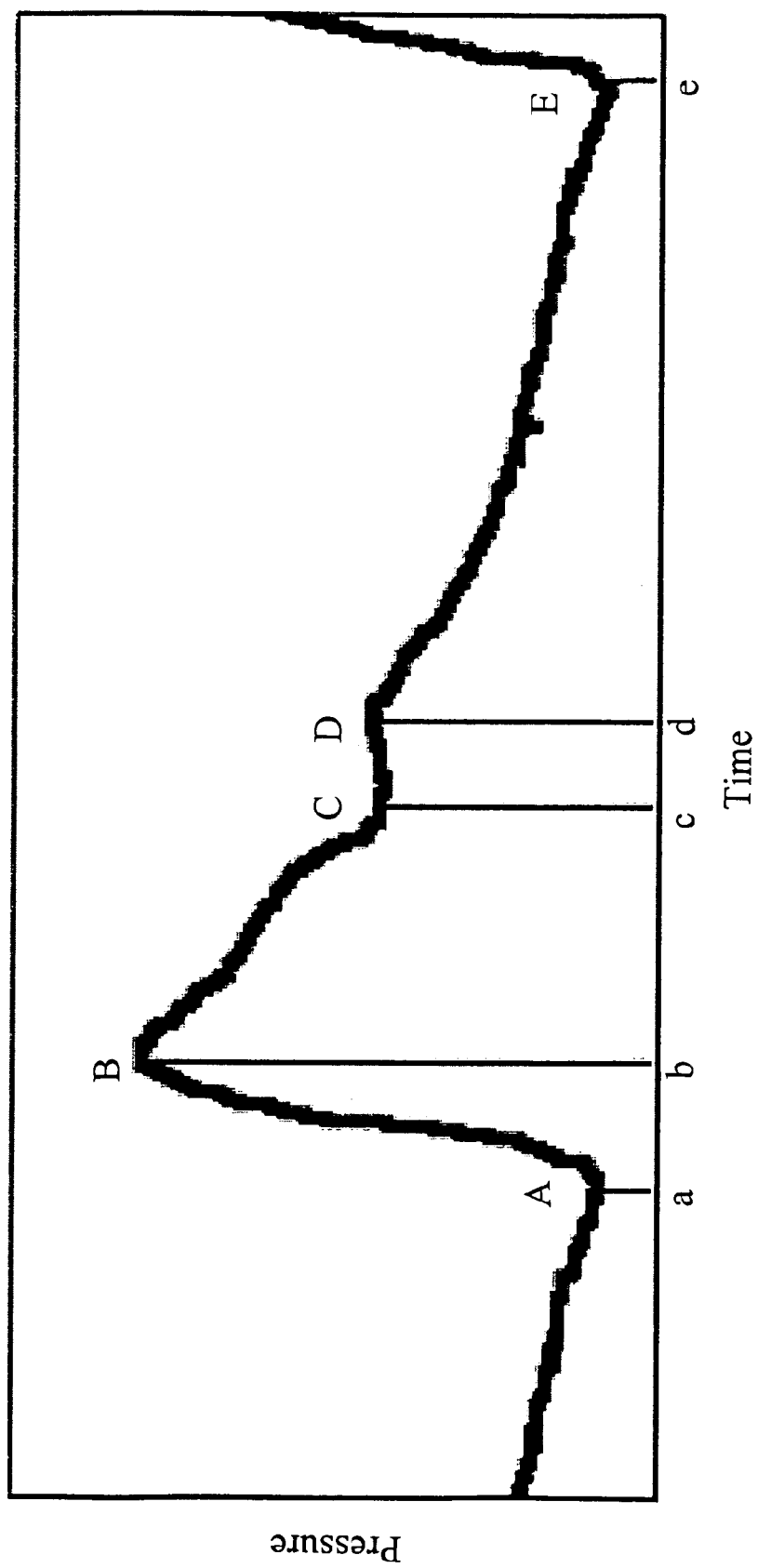
FIG. 3 illustrates an example of the blood pressure waveform of the hand radial artery of a senior/aged normal person.
Figure 4:
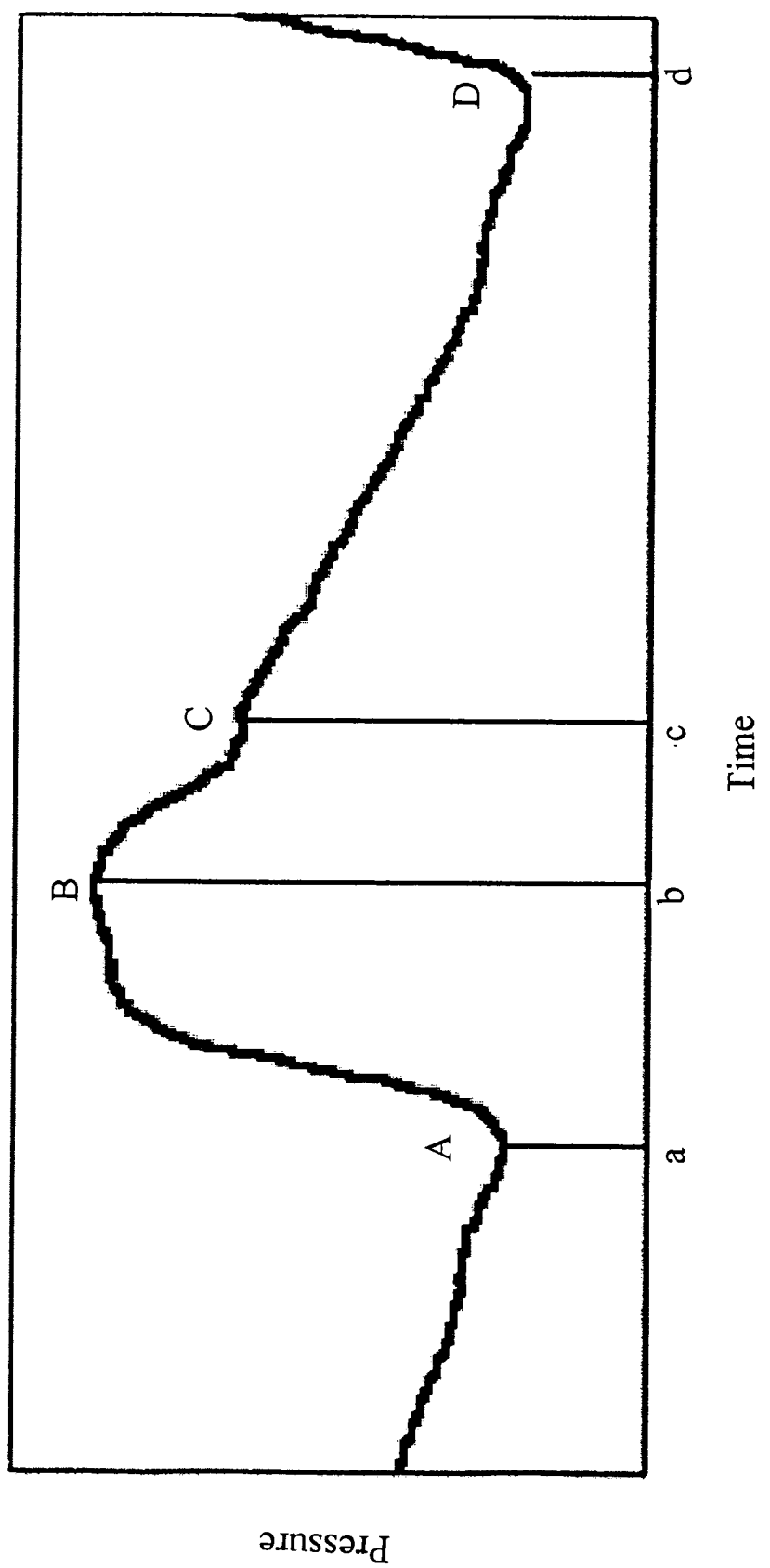
FIG. 4 illustrates an example of the blood pressure waveform of the hand radial artery of an acute hepatitis patient.

FIG. 3 illustrates the blood pressure wave shape blood pressure waveform of the hand radial artery of a typical senior person. The major difference between FIGS. 3 and 2 is that the second wave peak (points C, D and E in FIG. 2 and points B and C in FIG. 3) is not obvious and only displays a slight shoulder wave shape. It is generally inferred as being caused by the reduced artery elasticity of senior/aged persons, and therefore, the number of waveform peaks was reduced from 3 to 2. Otherwise, all parameters still can be clearly determined and calculated (see FIG. 3). There are many kinds of abnormal blood pressure waveforms. FIG. 4 illustrates the blood pressure waveform of the hand radius artery of an acute hepatitis patient, the wave peak number of which has been reduced to 1; with the exception of one broad major wave peak, the generated wave after the aorta valves are shut off only forms a shoulder wave, but not a wave peak (around point C). However, all parameters of the wave form can still be clearly determined and calculated.

According to the present invention, the hepatotoxicity or abnormal liver function generally represents that the examining indexes of liver function, such as the values of serum Glutamic Oxaloacetic Transaminase (SGOT, also known as AST), serum Glutamic Pyruvic Transaminase (SGPT, also known as ALT), alkaline phosphatase (ALK-P), r-Glutamyl Transpeptidase (r-GT), are higher or lower than the standard value recognized by international medical community or persons skilled in the art. For example, the standard value of SGPT is from 0 to 40, and therefore when the SGPT value is higher than the range, it indicates that the patient might have acute or chronic hepatitis, alcoholic liver injury, or cirrhosis of the liver.

According to the present invention, the sensors for measuring artery blood pressure waveforms can be, but are not limited to, a pressure sensing device. The pressure sensing device can be any conventional sensor for use in measure blood pressure waveform, such as a pressure sensor or a strain gauge. The structure of a pressure sensor can be, but is not limited to, a piezo-resistive or piezo-electrical pressure sensor. The sensing device can be placed on the skin surface near artery, such as the positions of head, neck, finger, wrist, forearm, buttocks, shoulder, thigh, leg, and foot. It is preferable that the pressure sensing device is an apparatus worn on wrist to measure the blood pressure waveform or blood pressure waveform of radial artery.

According to the present invention, the analyzer can be, but is not limited to, a small computer or an oscilloscope containing software and hardware elements, which can receive, storage, analyze, and show the blood pressure waveforms obtained from the sensors. The analyzers can use any conventional methods (e.g., De Boer et al. (1987), Yang et al. (1995) and ROC (Taiwan) Patent Publication No. 363, 404) to convert the blood pressure waveform obtained from sensors by known mathematical formulas and specific computer programs into parameters, such as the wave shape parameters, the time parameters, the pressure parameters, the oblique angle parameters, the superficial measure parameters, the ratio parameters and other wave characteristic parameters shown in FIGS. 2, 3 and 4, which can be mathematically defined and qualitatively and quantitatively described. Preferably, the device of software may record and compare the frequency changes of the parameters of blood pressure waveform of the patient in the period before and after taking the drug.

According to the present invention, the analyzer further comprises a display device to show the data and results recorded in the analyzer. The device can be, but is not limited to, a liquid crystal display device (LCD), an oscilloscope, a digital light-emitting diode(LED), a cathode-ray tube(CRT) or a printer.

According to the present invention, the analyzer further comprises an apparatus which can transfer the measured and analyzed data to a terminal at hospital's or doctor's end. In addition, the apparatus further comprises a signal delivering means for receiving signals transferred from the hospital or doctor. The signal delivering means can transfer signals in a wired or wireless way. The signals can be transferred by, for example, telephone, network satellite and wireless communication.

According to the present invention, if desired, the analyzer may comprise a warning device which can emit lyzer warnings signals. The warning signal can be a sound or light signal. The warning device can emit the warning signal based on the results obtained from the analyzer or the signal transferred from the hospital or by the doctor. The warning device can, but is not limited to, generate sound, show words or graphs by the display device, or show twinkling lights.

According to a preferred embodiment of the present invention, the non-invasive apparatus system for monitoring drug induced hapatotoxicity and abnormal liver function comprises:

an arm style blood pressure pulse wave gauge, which utilizes pressure sensing elements to transform the blood pressure pulse wave of the hand radius artery into wave shape parameters (including the number of wave peaks, the major wave peak point, the major wave trough point, the minor wave peak point, and/or the minor wave trough point), the time parameters, the pressure parameters, the oblique angle parameters, the superficial measure parameters, and/or the ratio parameters;

a bed-side recording analyzer, which can receive, amplify, filter, and transform between analog and digital signals from the electric wave of the blood pressure pulse gauge, wherein the analyzer comprises a small computer for recording the blood pressure pulse wave and analyze the frequency, the amplitude of vibration, and the angle; and an information server and a terminal machine to transmit the information from the analyzer to the hospital or clinic for medical examinations, and then instructions can be fed back by it to the patient's bed-side record analyzer.

The present invention also provides a method for monitoring the drug induced hepatotoxicity or abnormal liver function, which comprises utilizing the apparatus system of the present invention to monitor and calculate the blood pressure pulse wave shape parameters (including the number of wave peaks, the major wave peak point, the major wave trough point, the minor wave peak point, and the minor wave trough point), the time parameters, the pressure parameters, the oblique angle parameters, the superficial measure parameters, and/or the ratio parameters before and after taking the drug; if the altered amount of any parameter(s) before or after taking the drug is lower than a certain predetermined value, it represents that the drug has not induced a liver function side effect; if the altered amount of any parameter (s) is between two certain predetermined values, it represents that the drug has induced a certain level of change of liver function; if the altered amount of any parameter(s) is higher than a certain predetermined value, the drug has induced serious change on liver function.

According to a preferred embodiment of the present invention, the drug inducing abnormal liver function in a patient can be efficiently monitored and prevented by the following steps:

(I) periodically measuring all the blood pressure waveform parameters of the patient before and during the drug administration, wherein the periodical measurement can be proceeded daily, weekly or at any other time interval;

(II) calculating the degree of the functional change to the liver induced by taking the drug based on the data obtained from step (I), wherein the change comprises the altered amount of the blood pressure waveform wave form parameters, the time parameters, the pressure parameters, the oblique angle parameters, the superficial measure parameters and/or the ratio parameters before and after taking the drug; and (III) classifying the data obtained from step (II) into one of the following three types, which are defined based on the clinical trial data:
(a) the data being lower than a specific value represents that the drug is functioning normally;

(b) the data falling between two specific values represents that the drug has induced a functional change to the liver, the occurrence of the functional change needs to be strictly monitored, and a warning should be sent to the patient and/or the doctor; and (c) the data being higher than a specific value represents that a functional change to the liver induced by the drug has affected the patient's health and the patient should stop taking the drug immediately.

Figure 1:
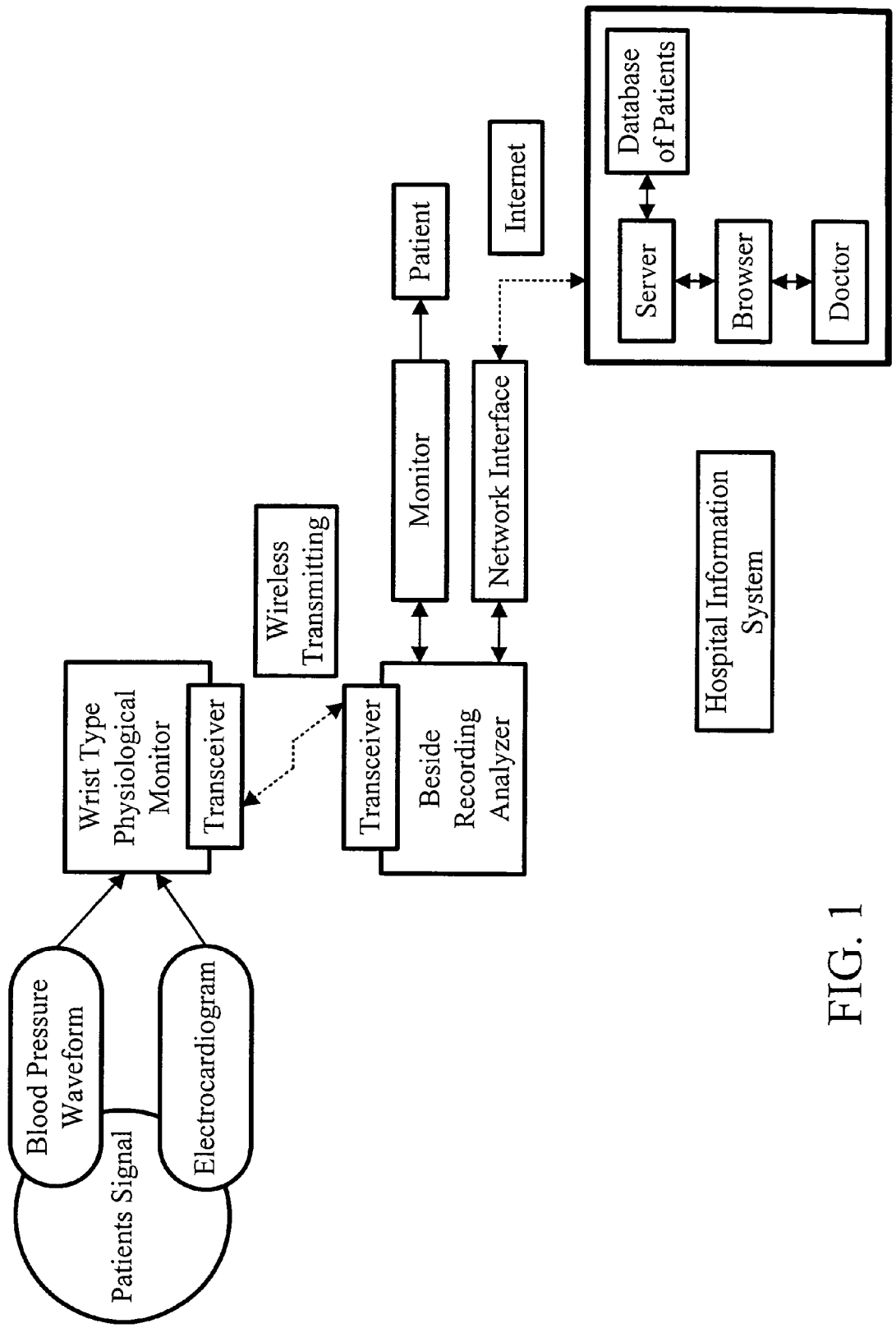
FIG. 1 illustrates a preferred embodiment of the invention.

According to the present invention, the method and apparatus system are provided for being used at home by patients, and the patients can be continuously monitored every day. The data obtains can be transferred to the doctor by the signal delivering means in the analyzer to inform the doctor of the patient's condition, and therefore further treatment to the patient if necessary, can be taken. Another preferred embodiment of the present invention is shown in FIG. 1. A wrist type sphygmomanometer using a pressure sensor transforms the patient's arterial radials blood pressure waveform to an electric wave. After the electric wave is amplified, filtered and analogy-digital transformed, it is delivered to a bedside analyzer. Said analyzer comprises a mini computer for recording the blood pressure waveform and analyzing all characteristic parameter values that represent liver function. The data will be shown by the displaying device of the analyzer and will be transferred to the patient's information server or the terminal at the hospital or clinic. The server or terminal will record, analyze and compare the data transferred from the patient's end, and will transfer the doctor's instructions to the bedside analyzer at the patient's end.

According to the monitoring system of the present invention, when a new drug is undergoing a human body clinical trial, the blood test of liver function (including the liver enzymes such as AST and ALT, and optionally Biliflavin) and the blood pressure waveform before or after the drug being administered should be examined. If the blood test values and the blood pressure waveform values are highly related (for example, if the AST and ALT values increase, it indicates that some characteristic parameters of the blood pressure waveform related to liver inflammation or poisoning should have comparatively increased or decreased), the data can be provided to the health authority to gain the authorization of using the non-invasive blood pressure waveform to replace the monthly (or bimonthly) blood test. When the drug is marketed, the drug-taking patients only need to use the monitoring system of the present invention to monitor and compare all the parameter values at home everyday. When the parameter values exceed the normal value range and reach a certain level (determined by the pharmaceutical company and doctor accord to the clinical values), the monitoring system will release an alarm signals to stop the patient from taking the drug, and the patient should take a complete liver function examination immediately.

All the equipments, apparatuses, and devices used in the apparatus system of the present invention described above are only examples for reaching the needed function. If other similar devices can accomplish a similar function, they can also be used in the apparatus system of the present invention. For example, measuring the human body blood pressure waveform can also be accomplished by measuring from other arteries rather than a radial artery; and the bedside record analyzer can also provide the side-effect alarm by pre-installed software, instead of sending the patient's information to the hospital or clinic; and the parameter definitions of all waveforms illustrated in FIGS. 2, 3 and 4 are but more obvious examples, other clear mathematical definitions which can describe the blood pressure waveform and its changes with quality and quantity can also be the parameters for monitoring.

The following examples further illustrate the applicability of the present invention so as to more substantiate the technical contents of the present invention. However, the examples are not provided for limiting the scope of the present invention. Different variations and modifications that can be achieved by persons skilled in the art based on the teachings of prior arts should all belong to the scope of the present invention.

EXAMPLE 1

Monitoring the Changed Liver Function Induced by the Drug—Dog Experiment

Two adult dogs weighing 12 and 15 kg were used. One (coded A) of them received 500 mg/kg of body weight of acetaminophen oral solution (dissolved in water); and the other one (coded B) received a higher concentration (1,200 mg/kg of body weight) of acetaminophen via subcutaneous injection. After Nembutal was injected and the respirator was put on, the hair on the front legs of the dogs was shaved and a blood pressure waveform sensor was inserted by operation. The waveform of artery blood pressure waveform on brachial position was continuously recorded and analyzed by a computer with a frequency of 100 data per minute. After surgery and before the drug was orally taken or injected, the blood pressure waveform of each dog was measured for two hours as the baseline. After the drug was orally taken or injected, the blood pressure waveform was continuously monitored for analyzing the hepatotoxicity induced by the drug, and blood samples were periodically taken from a tube inserted into the artery for determining the level of hepatotoxicuty. The results of the experiment are shown in TABLEs 1 to 8, and FIGS. 5 to 8.

TABLE 1

The Blood Test Results of Code A Dog

| Experimental conditions | Baseline | 1 hour after the drug was administered | 6 hours after the drug was administered | 12 hours after the drug was administered |
| --- | --- | --- | --- | --- |
| ASG (SGOT); IU/leter | 37 | 35 | 33 | 45 |
| ALT (SGPT); IU/leter | 28 | 25 | 23 | 24 |
| Total biliflavin MG/DL | 0.2 | 0.3 | 0.2 | 0.2 |

TABLE 2

The Analyzed Results Of All Parameter Values Of Blood Pressure Waveform Of Code A Dog (Before Taking The Drug - Baseline)

| Waveform parameters | Time parameter (second) | Pressure parameter (mmHg) | Oblique angle parameter (mmHg/sec.) | Superficial measure parameter (sec. * mmHg) | Ratio parameter |
|---|---|---|---|---|---|
| Number of wave peaks = 2 | T1 = ab = 0.06 | P1 = Aa = 148 | D1 = (Bb-Aa)/ab = 750 | A1 = AabB = 10 | RT1 = ab/ae = 0.16 |
| Major wave peak point = B | T2 = bc = 0.10 | P2 = Bb = 193 | D2 = (Bb-Cc)/bc = 390 | A2 = BbcC = 17 | RT2 = ac/ae = 0.42 |
| Major wave trough point = A or E | T3 = cd = 0.05 | P3 = Cc = 154 | D3 = (Dd-Cc)/cd = 300 | A3 = CcdD = 8 | RT3 = ad/ae = 0.55 |
| Minor wave peak point = D | T4 = de = 0.17 | P4 = Dd = 169 | D4 = (Dd-Ee)/de = 120 | A4 = DdeE = 27 | RP1 = Dd/Bb = 0.98 |
| Minor wave trough point = C | T5 = ae = 0.38 | P5 = Ee = 148 | D5 = D1 + D2 = 1140 | A5 = A1 + A2 = 27 | RA1 = A6/A5 = 1.30 |
| | | | D6 = D3 + D4 = 420 | A6 = A3 + A4 = 35 | RA2 = A5/A7 = 0.44 |
| | | | | A7 = A5 + A6 = 62 | RA3 = A6/A7 = 0.56 |

TABLE 3

The Analyzed Results Of All Parameter Values Of The Blood Pressure Waveform Of Code A Dog (12 Hours After Taking The Drug)

| Waveform parameters | Time parameter (second) | Pressure parameter (mmHg) | Oblique angle parameter (mmHg/sec.) | Superficial measure parameter (sec. * mmHg) | Ratio parameter |
|---|---|---|---|---|---|
| Number of wave peaks = 2 | T1 = ab = 0.05 | P1 = Aa = 149 | D1 = (Bb-Aa)/ab = 92 | A1 = AabB = 9 | RT1 = ab/ae = 0.12 |
| Major wave peak point = B | T2 = bc = 0.11 | P2 = Bb = 195 | D2 = (Bb-Cc)/bc = 350 | A2 = BbcC = 19 | RT2 = ac/ae = 0.40 |
| Major wave trough point = A or E | T3 = cd = 0.04 | P3 = Cc = 156 | D3 = (Dd-Cc)/cd = 420 | A3 = CcdD = 7 | RT3 = ad/ae = 0.49 |
| Minor wave peak point = D | T4 = de = 0.21 | P4 = Dd = 173 | D4 = (Dd-Ee)/de = 110 | A4 = DdeE = 34 | RP1 = Dd/Bb = 0.89 |
| Minor wave trough point = C | T5 = ae = 0.41 | P5 = Ee = 149 | D5 = D1 + D2 = 1270 | A5 = A1 + A2 = 28 | RA1 = A6/A5 = 1.46 |
| | | | D6 = D3 + D4 = 530 | A6 = A3 + A4 = 41 | RA2 = A5/A7 = 0.41 |
| | | | | A7 = A5 + A6 = 69 | RA3 = A6/A7 = 0.59 |

TABLE 4

The Analyzed Results Of All Parameter Altered Amounts Of The Blood Pressure Waveform Of Code A Dog Before And After Taking The Drug

| Waveform parameters | Time parameter Altered Amount (second) | Pressure parameter Altered amount (mmHg) | oblique angle parameter Altered amount (mmHg/sec.) | Superficial measure parameter Altered amount (sec. * mmHg) | Ratio parameter Altered amount |
|---|---|---|---|---|---|
| Number of wave peaks = 2 | T1 = ab = −16.7 | P1 = Aa = 0.7 | D1 = (Bb-Aa)/ab = 22.7 | A1 = AabB = −10.0 | RT1 = ab/ae = −25.0 |
| Major wave peak point = B | T2 = bc = 10.0 | P2 = Bb = 1.0 | D2 = (Bb-Cc)/bc = −10.2 | A2 = BbcC = 11.8 | RT2 = ac/ae = −5.0 |
| Major wave trough point = A or E | T3 = cd = −20.0 | P3 = Cc = 1.3 | D3 = (Dd-Cc)/cd = 40.0 | A3 = CcdD = −12.5 | RT3 = ad/ae = −11.0 |
| Minor wave peak point = D | T4 = de = 23.5 | P4 = Dd = 2.4 | D4 = (Dd-Ee)/de = −8.3 | A4 = DdeE = 25.9 | RP1 = Dd/Bb = 9.2 |
| Minor wave trough -point = C | T5 = ae = 7.9 | P5 = Ee = 0.7 | D5 = D1 + D2 = 11.4 | A5 = A1 + A2 = 3.7 | RA1 = A6/A5 = 12.3 |
| | | | D6 = D3 + D4 = 26.2 | A6 = A3 + A4 = 17.1 | RA2 = A5/A7 = −6.8 |
| | | | | A7 = A5 + A6 = 11.3 | RA3 = A6/A7 = 5.3 |

The definition of parameter altered amount is: (the parameter value after taking the drug—the parameter value before taking the drug)/the parameter value before taking the drug *100%

TABLE 5

Blood Test Results Of Code B Dog

| Experimental conditions | Base-line | 1 hour after the drug was administered | 6 hours after the drug was administered | 12 hours after the was administered |
|---|---|---|---|---|
| ASG (SGOT); IU/leter | 41 | 38 | 198 | 298 |

TABLE 5-continued

Blood Test Results Of Code B Dog

| Experimental conditions | Base-line | 1 hour after the drug was administered | 6 hours after the drug was administered | 12 hours after the was administered |
|---|---|---|---|---|
| ALT (SGPT); IU/leter | 32 | 33 | 37 | 47 |
| Total biliflavin MG/DL | 0.2 | 0.2 | 0.2 | 0.2 |

TABLE 6

The Analyzed Results Of All Parameter Values Of The Blood Pressure Waveform Of Code B Dog (Before Taking The Drug - Baseline)

| Waveform parameters | Time parameter (second) | Pressure parameter (mmHg) | Oblique angle parameter (mmHg/sec.) | Superficial measure parameter (sec. * mmHg) | Ratio parameter |
|---|---|---|---|---|---|
| Number of wave peaks = 3 | T1 = ab = 0.05 | P1 = Aa = 107 | D1 = (Bb-Aa)/ab = 860 | A1 = AabB = 6.4 | RT1 = ab/ae = 0.07 |
| Major wave peak point = B | T2 = bc = 0.04 | P2 = Bb = 150 | D2 = (Bb-Cc)/bc = 680 | A2 = BbcC = 5.5 | RT2 = ac/ae = 0.13 |
| Major wave trough point = A or G | T3 = cd = 0.04 | P3 = Cc = 123 | D3 = (Dd-Cc)/cd = 250 | A3 = CcdD = 5.1 | RT3 = ad/ae = 0.19 |
| Minor wave peak point = D&F 0.27 | T4 = de = 0.05 | P4 = Dd = 133 | D4 = (Dd-Ee)/de = 460 | A4 = DdeE = 6.1 | RT4 = ae/ag = 0.27 |
| Minor wave trough point = C & E | T5 = ae = 0.05 | P5 = Ee = 110 | D5 = D1 + D2 = 340 | A5 = EefF = 5.9 | RT5 = af/ag = 0.34 |
| | T6 = fg = 0.45 | P6 = Ff = 127 | D6 = D3 + D4 = 40 | A6 = FfgG = 52.7 | RP1 = Dd/Bb = 0.89 |
| | T7 = ag = 0.67 | P7 = Gg = 107 | D7 = D1 + D2 = 1540 | A7 = A1 + A2 = 11.9 | RP2 = Ef/Bb = 0.85 |
| | | | D8 = D3 + D4 = 710 | A8 = A3 + A4 = 11.2 | RA1 = A8/A7 = 0.94 |
| | | | D9 = D5 + D6 = 380 | A9 = A5 + A6 = 58.6 | RA2 = A9/A7 = 4.92 |
| | | | | A10 = A7 + A8 = 81.7 | RA3 = A7/A10 = 0.14 |
| | | | | | RA4 = A8/A10 = 0.14 |
| | | | | | RA5 = A9/A10 = 0.72 |

TABLE 7

The Analyzed Results Of All Parameter Values Of The Blood Pressure Waveform Of Code B Dog (12 Hours After Taking The Drug)

| Waveform parameters | Time parameter (second) | Pressure parameter (mmHg) | Oblique angle parameter (mmHg/sec.) | Superficial measure parameter (sec. * mmHg) | Ratio parameter |
|---|---|---|---|---|---|
| Number of wave peaks = 2 | T1 = ab = 0.04 | P1 = Aa = 16 | D1 = (Bb-Aa)/ab = 2250 | A1 = AabB = 2.44 | RT1 = ab/ag = 0.17 |
| Major wave peak point = B | T2 = be = 0.06 | P2 = Bb = 106 | D2 = (Bb-Ee)/be = 1383 | A2 = BbeE = 2.58 | RT2 = ae/ag = 0.42 |
| Major wave trough point = A or E | T3 = ef = 0.05 | P3 = Ee = 23 | D3 = (Ff-Ee)/ef = 420 | A3 = EefF = 1.68 | RT3 = af/ag = 0.63 |
| Minor wave peak point = F | T4 = fg = 0.09 | P4 = Ff = 44 | D4 = (Ff-Gg)/fg = 311 | A4 = FfgG = 2.70 | RP1 = Ff/Bb = 0.42 |
| Minor wave trough point = E | T5 = ag = 0.24 | P5 = Gg = 16 | D5 = D1 + D2 = 3633 | A5 = A1 + A2 = 5.02 | RA1 = A6/A5 = 0.87 |
| | | | D6 = D3 + D4 = 731 | A6 = A3 + A4 = 4.38 | RA2 = A5/A7 = 0.53 |
| | | | | A7 = A5 + A6 = 9.40 | RA3 = A6/A7 = 0.47 |

TABLE 8

The Analyzed Results Of All Parameter Altered Amounts Of The
Blood Pressure Waveform Of Code B Dog Before And After Taking The Drug

| Waveform parameters | Time parameter Altered amount (%) | Pressure parameter Altered amount (%) | Oblique angle parameter Altered amount (%) | Superficial measure parameter Altered amount (%) | Ratio parameter Altered amount (%) |
|---|---|---|---|---|---|
| Number of wave peaks = 2 | T1 = ab = −20 | P1 = Aa = −85 | D1 = (Bb-Aa)/ab = 162 | A1 = AabB = −62 | RT1 = ab/ag = 143 |
| Major wave peak point = B | T2 = be = −54 | P2 = Bb = −25 | D2 = (Bb-Ee)/be = 349 | A2 = BbeE = −85 | RT2 = ae/ag = 55 |
| Major wave trough point = A or E | T3 = ef = 0 | P3 = Ee = −79 | D3 = (Ff-Ee)/ef = 23 | A3 = EefF = −72 | RT3 = af/ag = 85 |
| Minor wave peak point = D | T4 = fg = −80 | P4 = Ff = −65 | D4 = (Ff-Gg)/fg = 677 | A4 = FfgG = −95 | RP1 = Ff/Bb = −51 |
| Minor wave trough point = C | T5 = ag = −64 | P5 = Gg = −85 | D5 = D1 + D2 = 211 | A5 = A1 + A2 = −47 | RA1 = A6/A5 = 123 |
| | | | D6 = D3 + D4 = 92 | A6 = A3 + A4 = −61 | RA2 = A5/A7 = 89 |
| | | | | A7 = A5 + A6 = −84 | RA3 = A6/A7 = −35 |

Figure 5:
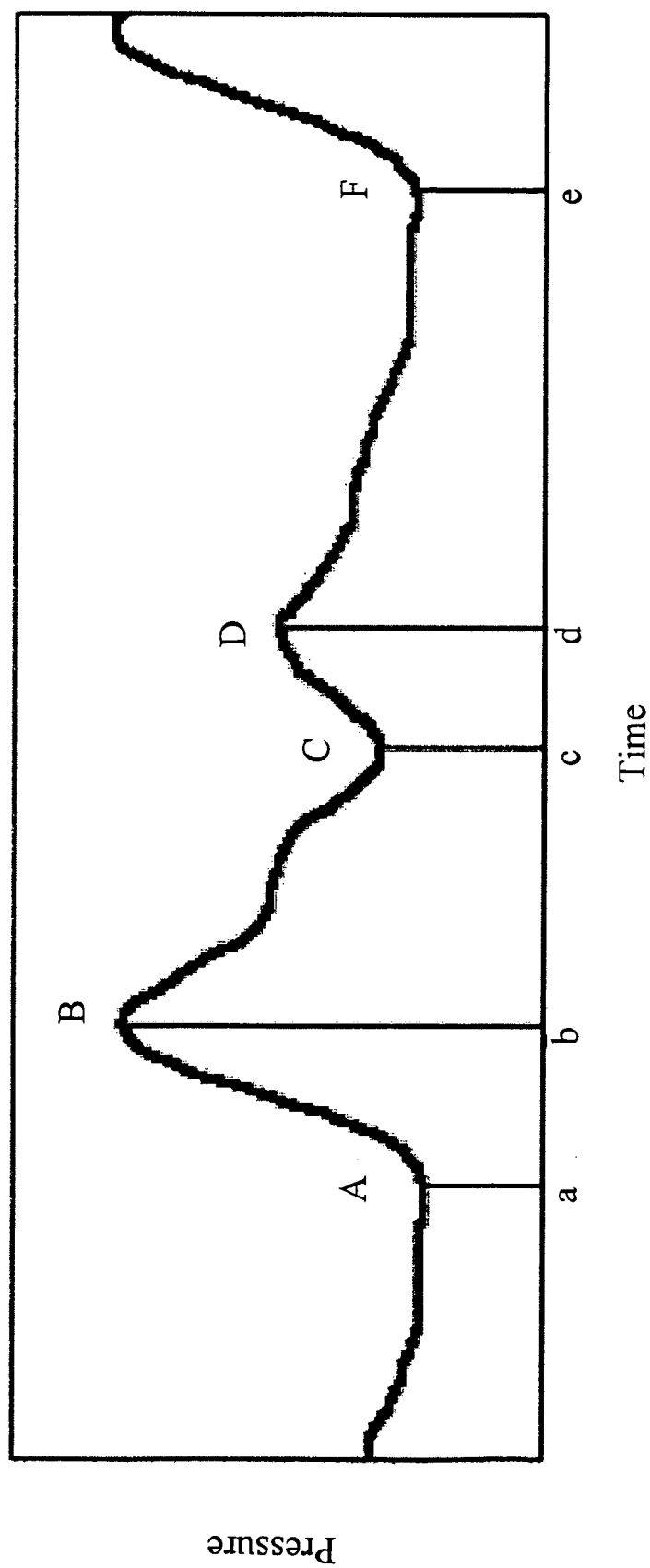
FIG. 5 illustrates the blood pressure waveform of the front leg artery of the dog coded A (before taking the drug base line)
Figure 6:
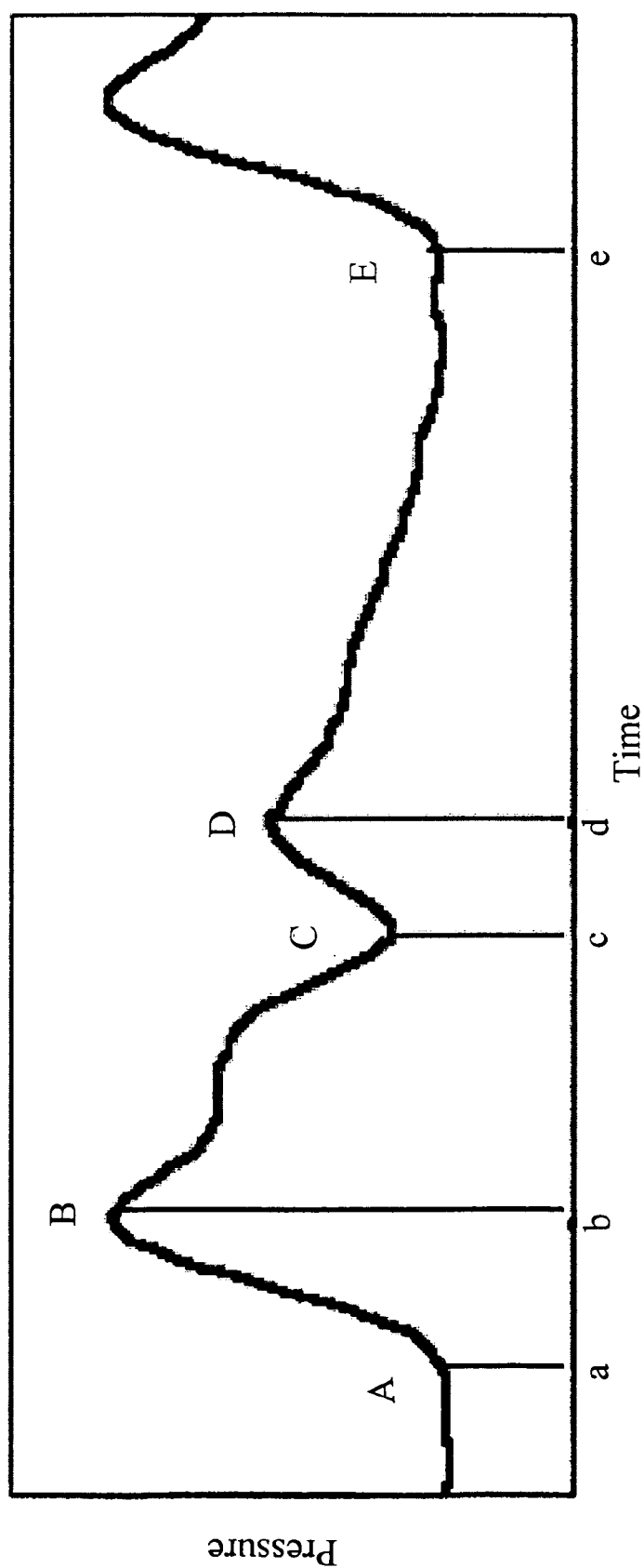
FIG. 6 illustrates the blood pressure waveform of the front leg artery of the dog coded A (12 hours after taking the drug acetaminophen)
Figure 7:
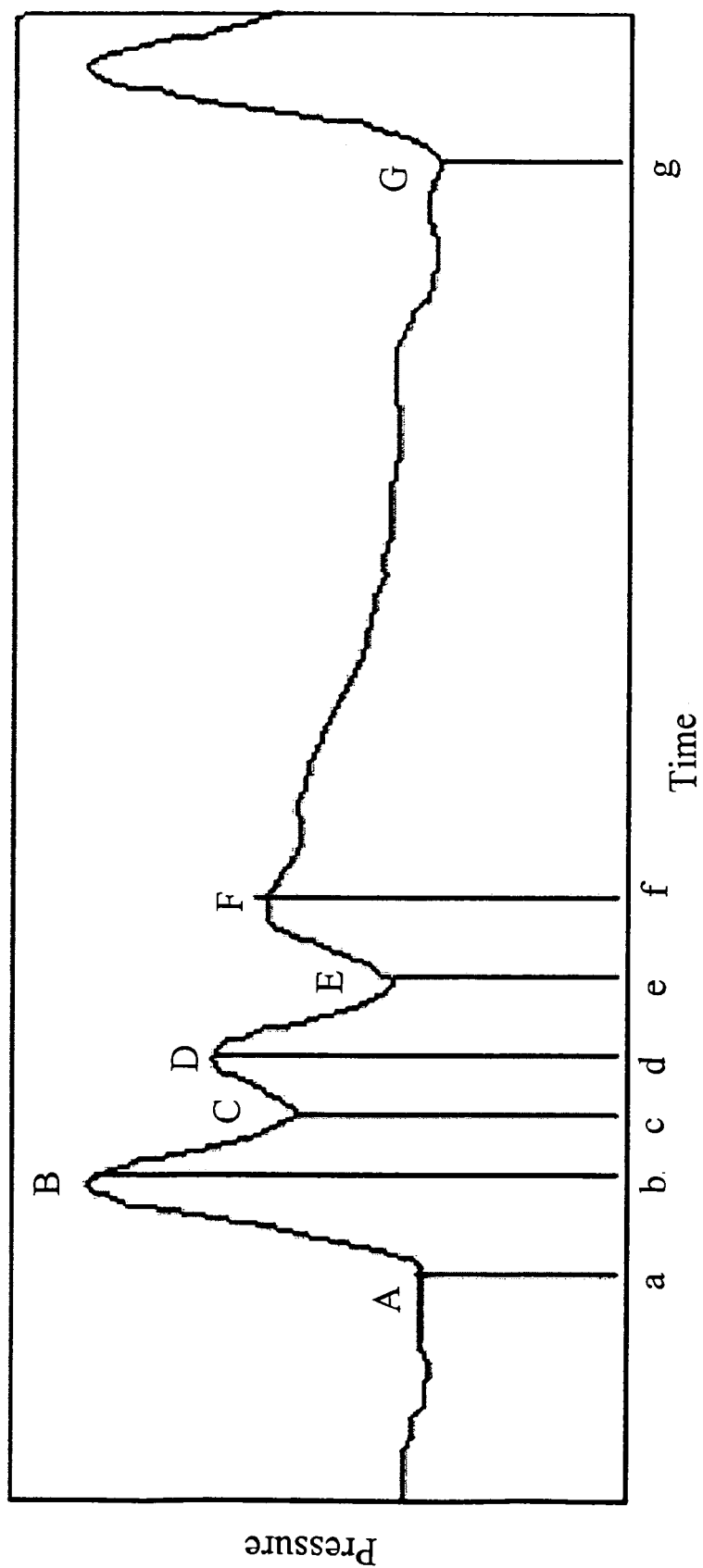
FIG. 7 illustrates the blood pressure waveform of the front leg artery of the dog coded B (before taking the drug-base line)

It is known that excessive consumption of the drug acetaminophen used in this experiment will cause the side effect of liver poisoning. Code A dog was fed orally with 500 mg/kg of the drug. Because of the digestion and absorption through the gastrointestinal organs, the effective dose of the drug in blood is lower. As shown in blood test results of TABLE 1, the toxicity of the drug to liver is very low, wherein the values of aspartate aminotransferase AST (SGOT), alanine aminotransferase ALT (SGOT) and biliflavin, which are most relevant to hepatotoxicity, do not deviate from the baseline, and the value of AST (SGOT) (the increased value may be caused by hepatocyte inflammation or other cell necosis) only increased slightly to 4.5 IU/liter after taking the drug for 12 hours. There is no significant difference between the blood pressure waveforms shown in FIG. 5, representing the dog's status before taking the drug and those shown in FIG. 6, representing the dog's status after taking the drug for 12 hours. The wave peak numbers of FIGS. 5 and 6 all show a number of 2, and the waveforms are almost the same. Similarly, when the blood pressure waveform parameters of Code A dog before taking the drug (TABLE 2) are compared with those of Code A after taking the drug (TABLE 3), the differences between them are not significant (see TABLE 4). Only the altered amount of the oblique angle parameter reaches 40%, and the altered amounts of the other parameters are all lower than this value.

Figure 8:
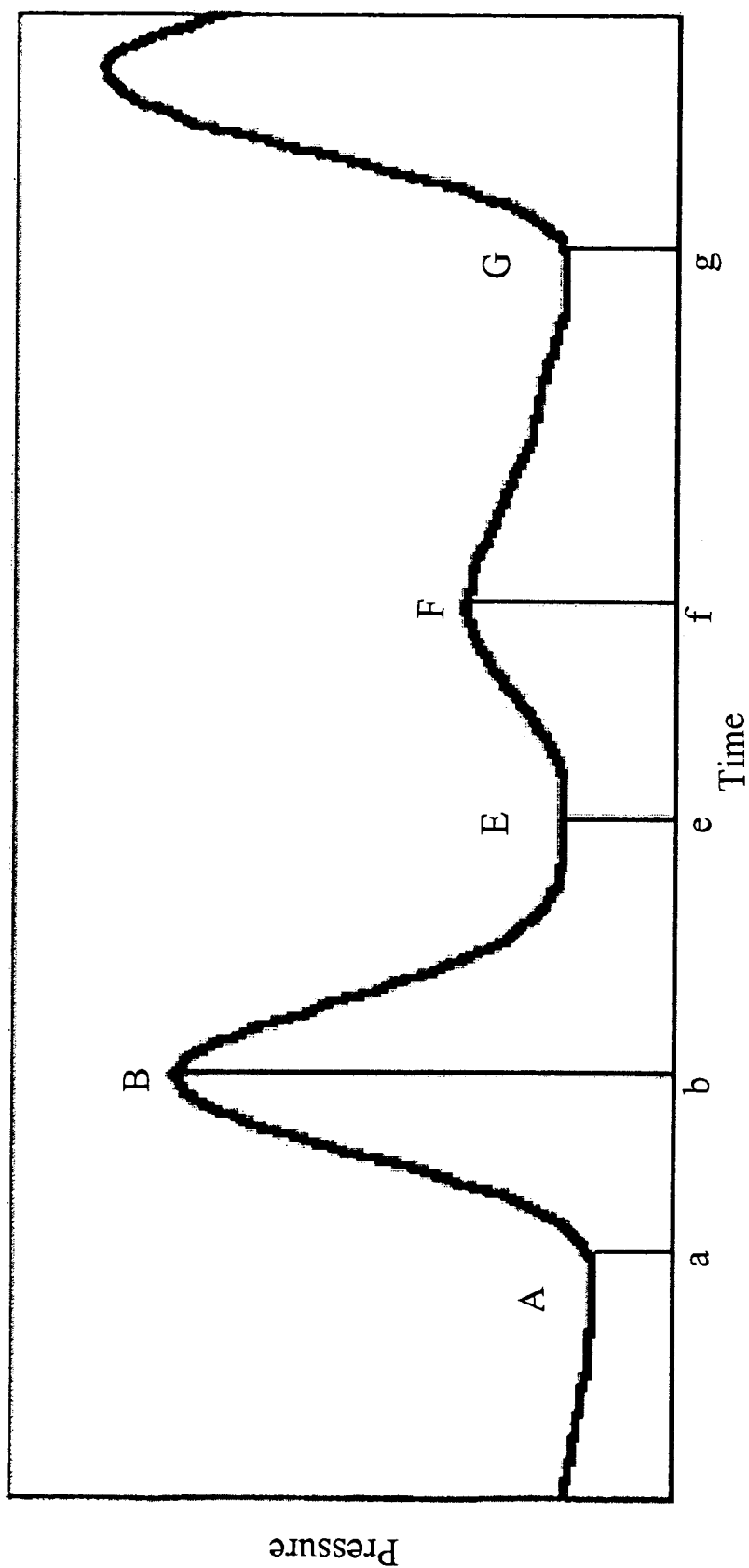
FIG. 8 illustrates the blood pressure waveform of the front leg artery of the dog coded B (12 hours after taking the drug acetaminophen)

On the other hand, Code B dog was given with the same drug in an amount of 1,200 mg/kg via subcutaneous injection. Because the drug can be effectively absorbed and the effective dose is higher in blood, the blood test results show a certain level of hapatotoxicity. After the drug has been taken for 12 hours, the value of AST (SGOT) raises from the baseline 41 (IU/liter) to 298 (IU/liter); the value of ALT also raises to 47. The value of biliflavin does not raise significantly because this is an acute poisoning experiment. A significant change can be found between the waveform before taking the drug (FIG. 7) and that after taking the drug for 12 hours (FIG. 8). The wave peak number (an important parameter for determining hepatotoxicity based on the clinical experiences) drops from 3 to 2. Comparing the blood pressure waveform parameters before taking the drug (TABLE 6) and those after taking the drug (TABLE 7), the altered amounts (TABLE 8) between them increase significantly than those of Code A dog. Among the blood pressure waveform parameters shown in TABLE 8, six altered amounts of the parameters exceed 100%. The result matches the result of the blood test, and means that the experiment of this example by analysing the comparison between the blood pressure waveforms before and after taking the drug can be used to monitor the hepatotoxicity induced by drugs, so as to send a alarm to the drug taking patient.

EXAMPLE 2

Monitoring the Hepatotoxicity Induced by Drugs—Clinical Trial of Human Body

Two middle-age patients had been diagnosed to have acute hepatitis induced by unknown drugs after being outpatient serviced or hospitalized. The hepatitis level of Code A patient was minor, and the value of ALT (SGOT) was 120 (IU/liter) when the patient was hospitalized, and then the value reduced to 42 (IU/liter) and close to a normal value after treatment, rest and recuperation. The physiological signals and the blood test results are shown in TABLE 9.

TABLE 9

The Physiological Signals And The Blood Test Results Of Code A Patient

| Experimental conditions | Morbidity period | After recovery |
|---|---|---|
| Pulse (beats/minute) | 76 | 65 |
| Systolic pressure (mmHg) | 110 | 105 |
| Diastolic pressure (mmHg) | 70 | 70 |
| Body temperature (° C., ear) | 36.5 | 36.0 |
| ALT (SGPT); IU/liter | 120 | 42 |
| Biliflavin MG/DL | 0.5 | 0.4 |

Another patient coded B had a more severe hepatitis level, and the value of ALT (SGOT) was 603 (IU/liter) when the patient was hospitalized, and the value reduced to 36 (IU/ liter) and to be close to a normal value after treatment and rest. The physiological signals and the blood test results are shown in TABLE 10.

TABLE 10

The Physiological Signals And The Blood Test Results Of Code B Patient

| Experimental conditions | Morbidity period | After recovery |
|---|---|---|
| Pulse (beats/minute) | 75 | 64 |
| Systolic pressure (mmHg) | 120 | 120 |
| Diastolic pressure (mmHg) | 80 | 80 |
| Body temperature (° C., ear) | 36.0 | 36.5 |
| ALT (SGPT); IU/liter | 603 | 36 |
| Biliflavin mg/dl | 2.5 | 0.3 |

These two patients also received a non-invasive blood pressure waveform measurment during the hospitalization period. The measure system comprises a pressure sensor (Entran Company in the United States, model EPN) wearing on the radial artery of the hand, a wrist type physiological monitor (made by the lab, composed by the following elements: an air pump, valves, a barometer, a receiving and processing device, a circuit, a central processing unit, a memory, and a wireless communicating device) to provide air pressure for the pressure sensors, a personal computer (containing a wireless receiving module and a software for receiving, storing and analysing blood pressure waveform), and a liquid crystal display (LCD) monitor.

Figure 9:
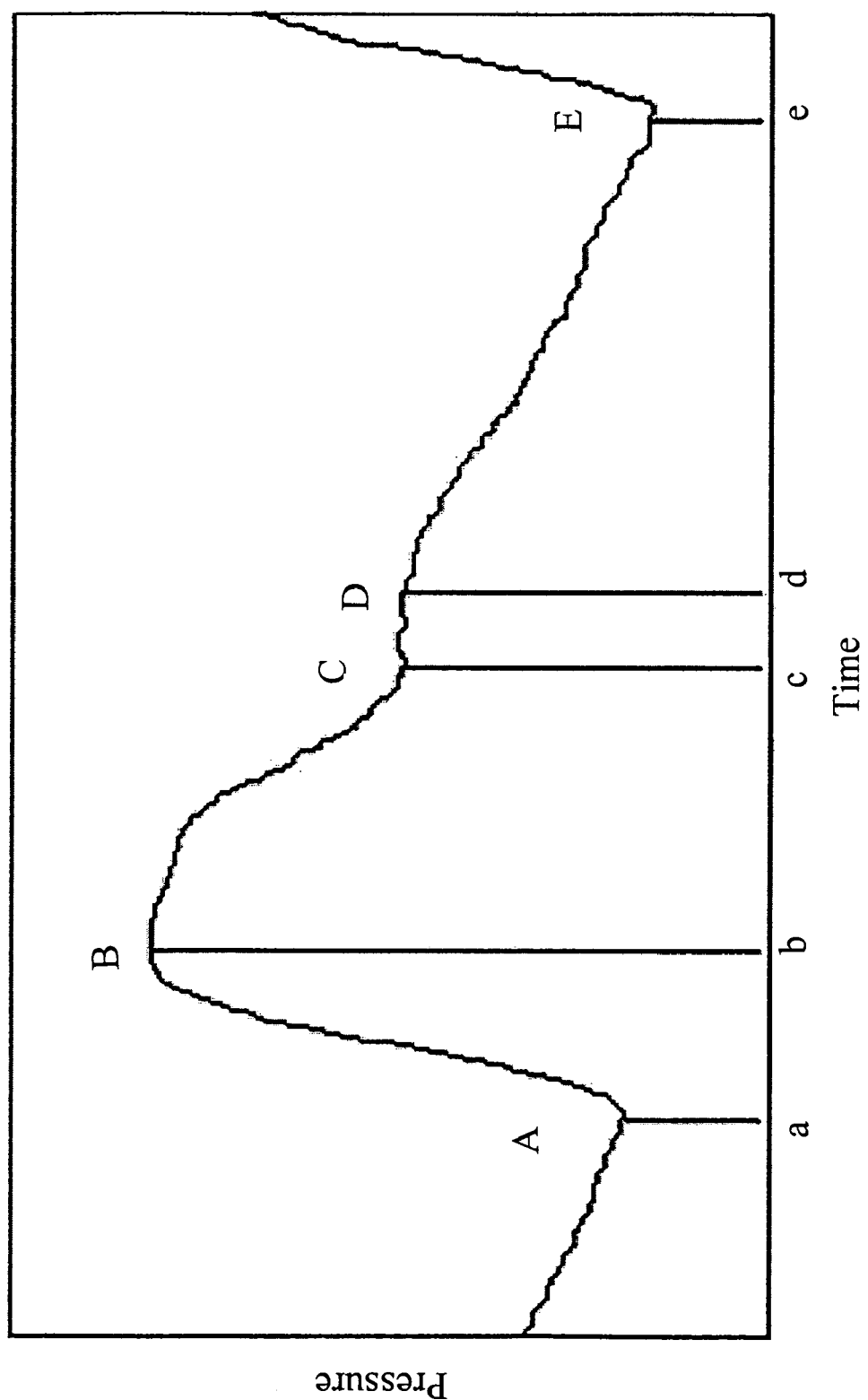
FIG. 9 illustrates the blood pressure waveform of the patient coded A during disease state of acute hepatitis.
Figure 10:
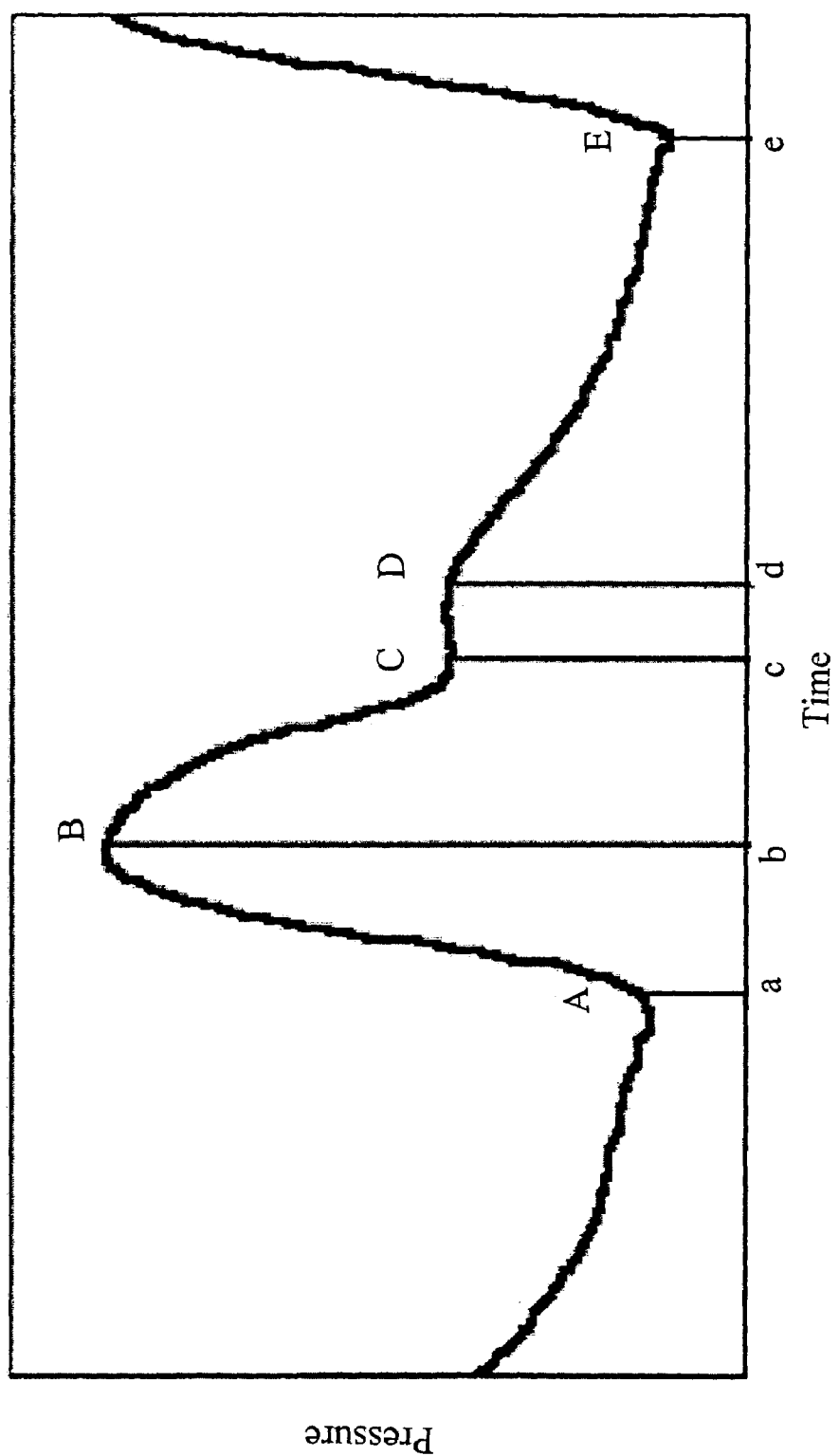
FIG. 10 illustrates the blood pressure waveform of the patient coded A after recovery from acute hepatitis.
Figure 11:
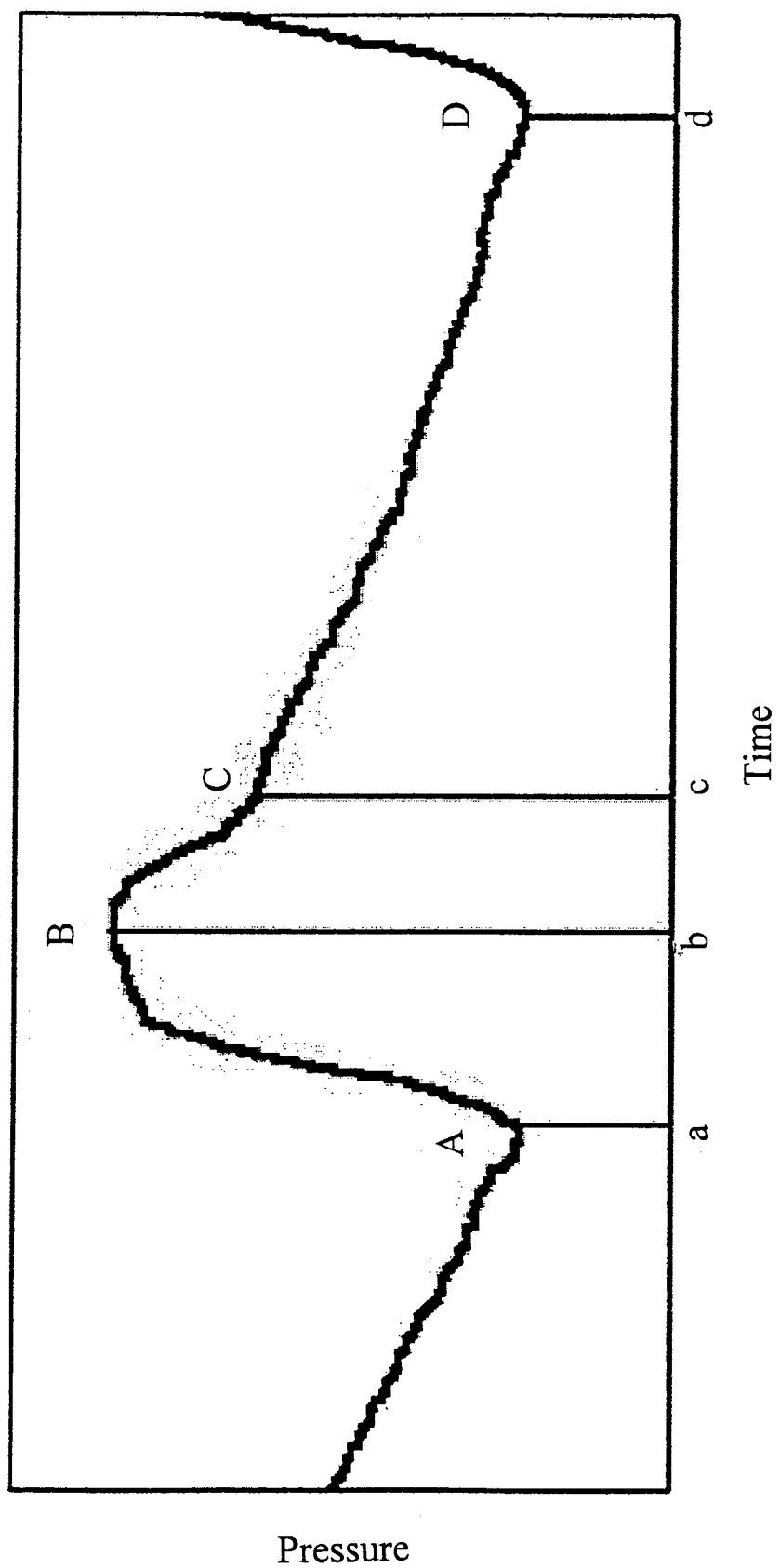
FIG. 11 illustrates the blood pressure waveform of the patient coded B during disease state of acute hepatitis.

The blood pressure waveform and the parameters of Code A patient in the morbidity period (measured on the day of hospitalization) are shown in FIG. 9 and TABLE 11, respectively. As compared with a normal senior person (FIG. 3), the blood pressure waveform of Code A patient is quite different. After resting in the hospital, the blood pressure waveform of the patient (FIG. 11) is getting close to a normal blood pressure waveform. Comparing the blood pressure waveform parameters of the morbidity period (TABLE 11) and the parameters after recovery (TABLE 12), a certain level of change can be found between them. However, according to the value of ALT (maximum 120 IU/liter) determined from the blood, the level of hepatitis is still low/insignificant. Generally, the clinical doctors will ask the patients to stop taking drugs, if the value of ALT increases 3 to 4 fold (90 to 130 IU/liter) than the normal value, and will strictly observe whether the hepatitis will gradually disappear or will become worse. Among the parameters listed in TABLE 13, the maximum altered amount is 110% (oblique angle parameter D4), but the altered amounts of the pressure parameter (1 to 8%) and the altered amounts of ratio parameter (2 to 24%) are still in a minor range. According to the clinical data of the patient and those of 5 other similar cases, it is suggested that the altered amounts of blood pressure waveform with this level represent the obvious existence of liver poisoning, and that an alarm should be sent to doctors and patients to consider whether the patient should stop taking all kinds of drugs.

TABLE 11

The Analyzed Results Of All Parameter Values Of The Blood Pressure Waveform Of Code A Patient During Morbidity Period

| Waveform parameters | Time parameter (second) | Pressure parameter (mmHg) | Oblique angle parameter (mmHg/sec.) | Superficial measure parameter (sec. * mmHg) | Ratio parameter |
|---|---|---|---|---|---|
| Number of wave peaks = 2 | T1 = ab = 0.17 | P1 = Aa = 69 | D1 = (Bb-Aa)/ab = 235 | A1 = AabB = 15 | RT1 = ab/ae = 0.22 |
| Major wave peak point = B | T2 = bc = 0.19 | P2 = Bb = 109 | D2 = (Bb-Cc)/bc = 100 | A2 = BbcC = 19 | RT2 = ac/ae = 0.46 |
| Major wave trough point = A or E | T3 = cd = 0.07 | P3 = Cc = 90 | D3 = (Dd-Cc)/cd = 14 | A3 = CcdD = 6 | RT3 = ad/ae = 0.54 |
| Minor wave peak point = D | T4 = de = 0.36 | P4 = Dd = 91 | D4 = (Dd-Ee)/de = 61 | A4 = DdeE = 29 | RP1 = Dd/Bb = 0.83 |
| Minor wave trough point = C | T5 = ae = 0.79 | P5 = Ee = 69 | D5 = D1 + D2 = 335 | A5 = A1 + A2 = 34 | RA1 = A6/A5 = 1.03 |
| | | | D6 = D3 + D4 = 75 | A6 = A3 + A4 = 35 | RA2 = A5/A7 = 0.49 |
| | | | | A7 = A5 + A6 = 69 | RA3 = A6/A7 = 0.51 |

TABLE 12

The Analyzed Results Of All Parameter Values Of The Blood Pressure Waveform Of Code A Patient After Recovery

| Waveform parameters | Time parameter (second) | Pressure parameter (mmHg) | Oblique angle parameter (mmHg/sec.) | Superficial measure parameter (sec. * mmHg) | Ratio parameter |
|---|---|---|---|---|---|
| Number of wave peaks = 2 | T1 = ab = 0.17 | P1 = Aa = 70 | D1 = (Bb-Aa)/ab = 200 | A1 = AabB = 15 | RT1 = ab/ae = 0.18 |
| Major wave peak point = B | T2 = bc = 0.19 | P2 = Bb = 104 | D2 = (Bb-Cc)/bc = 111 | A2 = BbcC = 18 | RT2 = ac/ae = 0.39 |
| Major wave trough point = A or E | T3 = cd = 0.09 | P3 = Cc = 83 | D3 = (Dd-Cc)/cd = 11 | A3 = CcdD = 8 | RT3 = ad/ae = 0.49 |

TABLE 12-continued

The Analyzed Results Of All Parameter Values Of The Blood
Pressure Waveform Of Code A Patient After Recovery

| Waveform parameters | Time parameter (second) | Pressure parameter (mmHg) | Oblique angle parameter (mmHg/sec.) | Superficial measure parameter (sec. * mmHg) | Ratio parameter |
|---|---|---|---|---|---|
| Minor wave peak point = D | T4 = de = 0.48 | P4 = Dd = 84 | D4 = (Dd-Ee)/de = 29 | A4 = DdeE = 37 | RP1 = Dd/Bb = 0.81 |
| Minor wave trough point = C | T5 = ae = 0.92 | P5 = Ee = 70 | D5 = D1 + D2 = 311 | A5 = A1 + A2 = 33 | RA1 = A6/A5 = 1.36 |
|  |  |  | D6 = D3 + D4 = 40 | A6 = A3 + A4 = 45 | RA2 = A5/A7 = 0.42 |
|  |  |  |  | A7 = A5 + A6 = 78 | RA3 = A6/A7 = 0.58 |

TABLE 13

The Analyzed Results Of All Parameter Altered Amounts Of The
Blood Pressure Waveform Of Code A Patient Before And After The Existence Of Hepatitis

| Time parameter Altered amount (%) | Pressure parameter Altered amount (%) | Oblique angle parameter Altered amount (%) | Superficial measure parameter Altered amount (%) | Ratio parameter Altered amount (%) | Time parameter Altered amount (%) |
|---|---|---|---|---|---|
| Number of wave peaks = 2 | T1 = ab = 0 | P1 = Aa = 1 | D1 = (Bb-Aa)/ab = 18 | A1 = AabB = 0 | RT1 = ab/ae = 22 |
| Major wave peak point = B | T2 = bc = 0 | P2 = Bb = 5 | D2 = (Bb-Cc)/bc = −10 | A2 = BbcC = 6 | RT2 = ac/ae = 18 |
| Major wave trough point = A or E | T3 = cd = −22 | P3 = Cc = 8 | D3 = (Dd-Cc)/cd = 27 | A3 = CcdD = −25 | RT3 = ad/ae = 10 |
| Minor wave peak point = D | T4 = de = −25 | P4 = Dd = 8 | D4 = (Dd-Ee)/de = 110 | A4 = DdeE = −22 | RP1 = Dd1 = Bb = 2 |
| Minor wave trough point = C | T5 = ae = −14 | P5 = Ee = −1 | D5 = D1 + D2 = 8 | A5 = AL + A2 = 3 | RA1 = A6/A5 = −24 |
|  |  |  | D6 = D3 + D4 = 88 | A6 = A3 + A4 = −22 | RA2 = A5/A7 = 17 |
|  |  |  |  | A7 = A5 + A6 = −12 | RA3 = A6/A7 = −12 |

Figure 12:
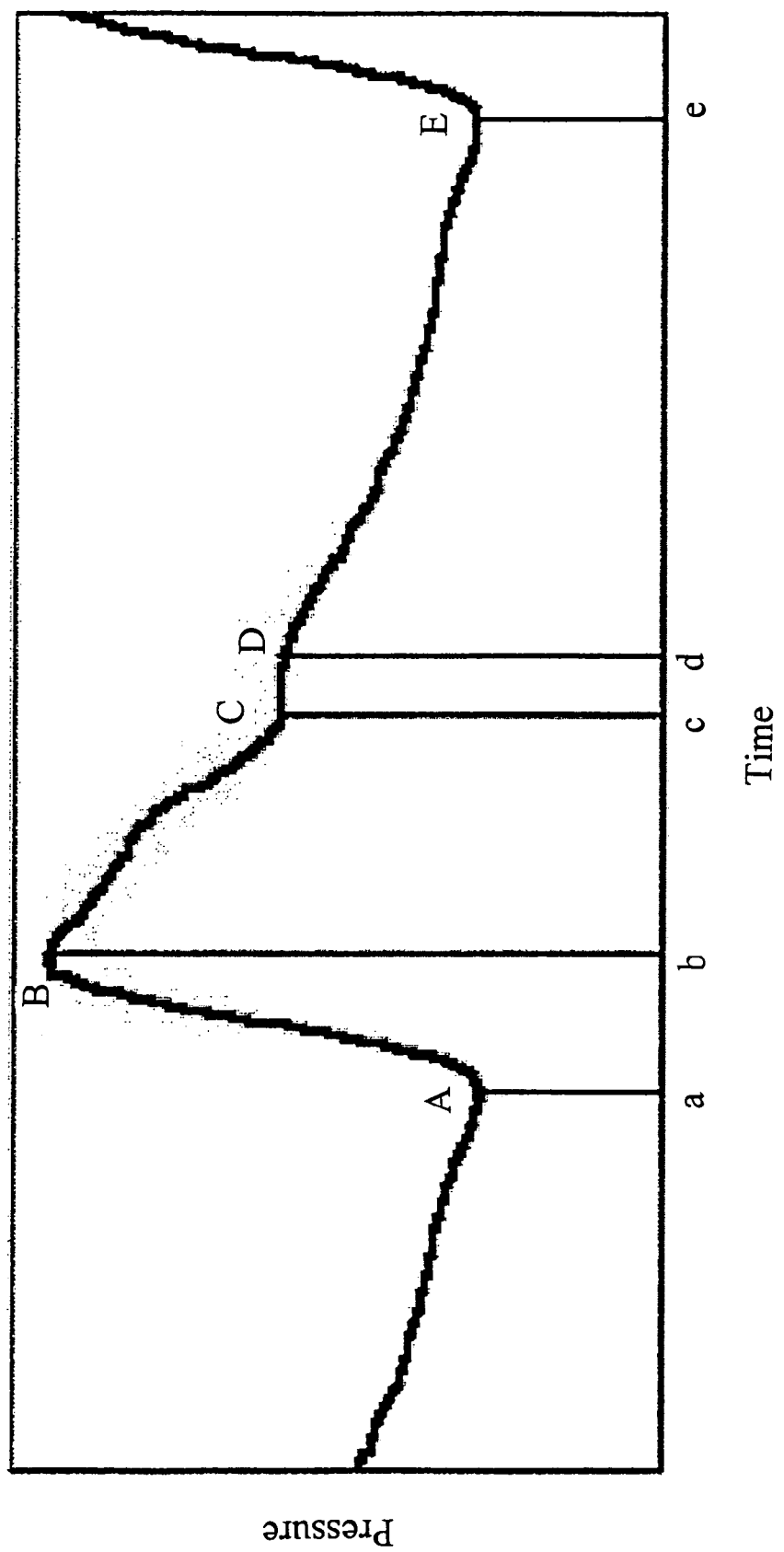
FIG. 12 illustrates the blood pressure waveform of the patient coded B after recovery from acute hepatitis.

The definition of the parameter altered amounts is: (the parameter value of morbidity period−the parameter value of recovered)/ the parameter value of recovered *100%. After comparing and analysing the blood pressure waveforms of the Code B patient during morbidity period (FIG. 11 and TABLE 14) and after recovery (FIG. 12 and TABLE 15), the results (TABLE 16) show that Code B patient had a more severe level of liver poisoning in comparison with Code A patient, and the wave peak number (an important parameter of liver side effect) reduces from the number of 2 of the normal period (i.e,. after recovery) to the number of 1 of the morbidity period. In addition, among the parameter altered amounts listed in TABLE 16, there are three altered amounts equaling to or exceeding 100%. The result meets that obtained from the blood test. According to the clinical data of the patient and those of other similar cases, it is suggested that the altered amounts of blood pressure waveform with this level represent the existence of a severe liver side effect, and that the patient should stop taking all kinds of drugs and should be treated.

TABLE 14

The Analyzed Results Of All Parameter Values Of The Blood
Pressure Waveform Of Code B Patient During Morbidity Period

| Waveform parameters | Time parameter (second) | Pressure parameter (mmHg) | Oblique angle parameter (mmHg/sec.) | Superficial measure parameter (sec. * mmHg) | Ratio parameter |
|---|---|---|---|---|---|
| Number of wave peaks = 2 | T1 = ab = 0.22 | P1 = Aa = 80 | D1 = (Bb-Aa)/ab = 182 | A1 = AabB = 22 | RT1 = ab/ad = 0.28 |
| Major wave peak point = B | T2 = bc = 0.13 | P2 = Bb = 120 | D2 = (Bb-Cc)/bc = 115 | A2 = BbcC = 15 | RT2 = ac/ad = 0.44 |
| Major wave trough point = A or D | T3 = cd = 0.45 | P3 = Cc = 105 | D3 = D1 + D2 = 297 | A3 = CcdD = 42 | RA1 = A3/A4 = 1.14 |
| Minor wave trough point = C | T4 = ad = 0.8 | P4 = Dd = 80 |  | A4 = A1 + A2 = 37 | RA2 = A4/A5 = 0.47 |
|  |  |  |  | A5 = A3 + A4 = 79 | RA3 = A3/A5 = 0.53 |

TABLE 15

Blood Pressure Waveform of Code B patient during recovery period
The analyzed results of all parameter values

| Waveform parameters | Time parameter (second) | Pressure parameter (mmHg) | oblique angle parameter (mmHg/sec.) | Superficial measure parameter (sec. * mmHg) | Ratio parameter |
|---|---|---|---|---|---|
| Number of wave peaks = 2 | T1 = ab = 0.11 | P1 = Aa = 80 | D1 = (Bb − Aa)/ab = 364 | A1 = AabB = 11 | RT1 = ab/ae = 0.12 |
| Major wave peak point = B | T2 = bc = 0.23 | P2 = Bb = 120 | D2 = (Bb − Cc)/bc = 91 | A2 = BbcC = 25 | RT2 = ac/ae = 0.36 |
| Major wave trough point = A or E | T3 = cd = 0.07 | P3 = Cc = 99 | D3 = (Dd − Cc)/cd = 0 | A3 = CcdD = 7 | RT3 = ad/ae = 0.44 |
| Minor wave peak point = D | T4 = de = 0.53 | P4 = Dd = 99 | D4 = (Dd − Ee)/de = 36 | A4 = DdeE = 47 | RP1 = Dd/Bb = 0.83 |
| Minor wave trough point = C | T5 = ae = 0.94 | P5 = Ee = 80 | D5 = D1 + D2 = 455 | A5 = A1 + A2 = 36 | RA1 = A6/A5 = 1.5 |
|  |  |  | D6 = D3 + D4 = 36 | A6 = A3 + A4 = 54 | RA2 = A5/A7 = 0.4 |
|  |  |  |  | A7 = A5 + A6 = 90 | RA3 = A6/A7 = 0.6 |

TABLE 16

The Analyzed Results Of All Parameter Altered Amounts Of The
Blood Pressure Waveform Of Code B Patient Before And After
The Existence Of Hepatitis

| Time parameter Altered amount (%) | Pressure parameter Altered amount (%) | Oblique angle parameter Altered amount (%) | Superficial measure parameter Altered amount (%) | Ratio parameter Altered amount (%) | Time parameter Altered amount (%) |
|---|---|---|---|---|---|
| Number of wave peaks = 2 | T1 = ab = 100 | P1 = Aa = 0 | D1 = (Bb − Aa)/ab = −50 | A1 = AabB = 100 | RT1 = ab/ad = 133 |
| Major wave peak point = B | T2 = bc = −43 | P2 = Bb = 0 | D2 = (Bb − Cc)/bc = 26 | A2 = BbcC = −40 | RT2 = ac/ad = 22 |
| Major wave trough point = A | T3 = cd = −25 | P3 = Cc = 6 | D3 = D1 + D2 = −40 | A3 = CcdD = 17 | RA1 = A3/A4 = −24 |
| Minor wave trough point = C | T4 = ad = −15 | P4 = Dd = 0 |  | A4 = A1 + A2 = 3 | RA2 = A4/A5 = 18 |
|  |  |  |  | A5 = A3 + A4 = −12 | RA3 = A3/A5 = −12 |

Note:
(1) The definition of parameter altered amounts is: (the parameter value of morbidity period-the parameter value of recovered status)/the parameter value of recovered status * 100%;
(2) The parameter altered amount (T3) is calculated from the comparison between the parameter value of recovered status [T3 + T4 (= 0.60)] and the parameter value of morbidity period [T3 (= 0.45)] to meet the original definition of the parameter altered amounts;
(3) The parameter altered amount (T4) is calculated from the comparison between the parameter value of recovered status [T5 (= 0.94)] and the parameter value of morbidity period [T3 (= 0.80)] to meet the original definition of the parameter altered amounts;
(4) The parameter altered amount (D3) is calculated from the comparison between the parameter value of recovered status [D5 (= 455)] and the parameter value of morbidity period [D3 (= 297)] to meet the original definition of the parameter altered amounts;
(5) The parameter altered amount (A3) is calculated from the comparison between the parameter value of recovered status [A5 (= 36)] and the parameter value of morbidity period [A3 (= 42)], to meet the original definition of the parameter altered amounts;
(6) The parameter altered amount (A4) is calculated from the comparison between the parameter value of recovered status [A5 (= 36)] and the parameter value of morbidity period [A4 (= 37)], to meet the original definition of the parameter altered amounts;
(7) The parameter altered amount (A5) is calculated from the comparison between the parameter value of recovered status [A7 (= 90)] and the parameter value of morbidity period [A5 (= 79)], to meet the original definition of the parameter altered amounts;

What is claimed is:

1. A non-invasive apparatus system for monitoring drug hepatotoxicity or drug-induced abnormal liver function comprising:
   (a) a sensor for measuring artery blood pressure waveforms to form electric waves representing the artery blood pressure waveforms; and
   (b) an analyzer for receiving the electric waves from (a), the electric waves obtained before and after drug intake being calculated by mathematical formulas; wherein if any altered amounts of any or some of the electric waves are between two certain preset values or higher than a preset value, the analyzer determines that the drug has induced a certain level of liver function change or the drug has induced a severe liver function change; and then a warning device comprised in the analyzer will emit warning signals.

2. The apparatus system according to claim 1, wherein the sensor is a pressure sensory device or one or more electrode chips.

3. The apparatus system according to claim 2, wherein the pressure sensory device is an apparatus worn on wrist to measure the blood pressure waveform of radial artery.

4. A method for monitoring drug hepatotoxicity or drug-induced abnormal liver function, the method comprising utilizing the apparatus system of claim 3.

5. A method for monitoring drug hepatotoxicity or drug-induced abnormal liver function, the method comprising utilizing the apparatus system of claim 2.

6. The apparatus system according to claim 1, wherein the analyzer further comprises a display device for showing the analyzing data and results recorded in the analyzer.

7. A method for monitoring drug hepatotoxicity or drug-induced abnormal liver function, the method comprising utilizing the apparatus system of claim 6.

8. The apparatus system according to claim 1, wherein the analyzer further comprises an apparatus, which can transfer the measured and analyzed data to a terminal at hospital's or doctor's end, and the apparatus can further receive the signals transferred from the hospital or doctor.

9. A method for monitoring drug hepatotoxicity or drug-induced abnormal liver function, the method comprising utilizing the apparatus system of claim 8.

10. The apparatus system according to claim 8, wherein the signal is transferred in a wired or wireless way.

11. A method for monitoring drug hepatotoxicity or drug-induced abnormal liver function, the method comprising utilizing the apparatus system of claim 10.

12. A method for monitoring drug hepatotoxicity or drug-induced abnormal liver function, the method comprising utilizing the apparatus system of claim 1.

13. The apparatus system according to claim 1, wherein the electric waves comprise waveform parameters including a number of wave peaks, a major wave peak point, a major wave trough point, a minor wave peak point, and/or a minor trough point, time parameters, pressure parameters, oblique angle parameters, superficial measure parameters, and/or ratio parameters.

14. A method for monitoring drug hepatotoxicity or drug-induced abnormal liver function, the method comprising utilizing the apparatus system of claim 13.

15. A non-invasive apparatus system for monitoring drug hepatotoxicity or drug-induced abnormal liver function comprising:

a wrist type sphygmomanometer which uses a pressure sensory element to transform radial artery blood pressure waveform of a patient's arm to electric waves;

a bedside recording analyzer which can receive, amplify, filter, and analog-digital transform the electric waves from the sphygmomanometer, wherein the analyzer comprises a small computer to record and analyze the electric waves obtained before and after drug intake by mathematical formulas; wherein if any altered amounts of any or some of the electric waves are between two certain preset values or higher than a preset value, the drug has induced a certain level of liver function change or the drug has induced a severe liver function change; and an information server and a terminal machine which can send the information from the analyzer to a hospital or clinic for a doctor's diagnosis, and send back instructions from the doctor to the patient's bedside record analyzer.

16. A method for monitoring drug hepatotoxicity or drug-induced abnormal liver function, the method comprising utilizing the apparatus system of claim 15.

17. The apparatus system according to claim 15, wherein the electric waves comprise waveform parameters including a number of wave peaks, a major wave peak point, a major wave trough point, a minor wave peak point, and/or a minor trough point, time parameters, pressure parameters, oblique angle parameters, superficial measure parameters, and/or ratio parameters.

18. A method for monitoring drug hepatotoxicity or drug-induced abnormal liver function, the method comprising utilizing the apparatus system of claim 17.

* * * * *